United States Patent
Khismatullin et al.

(10) Patent No.: US 10,823,723 B2
(45) Date of Patent: Nov. 3, 2020

(54) APPARATUS, SYSTEMS AND METHODS FOR INTEGRATIVE PHOTO-OPTICAL/MECHANICAL TEST FOR NONCONTACT MEASUREMENT OF POLYMERIZATION

(71) Applicant: The Administrators of the Tulane Education Fund, New Orleans, LA (US)

(72) Inventors: Damir Khismatullin, New Orleans, LA (US); Daishen Luo, Metairie, LA (US)

(73) Assignee: The Administration of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 16/478,249

(22) PCT Filed: Jan. 23, 2018

(86) PCT No.: PCT/US2018/014879
§ 371 (c)(1),
(2) Date: Jul. 16, 2019

(87) PCT Pub. No.: WO2018/136949
PCT Pub. Date: Jul. 26, 2018

(65) Prior Publication Data
US 2019/0353637 A1    Nov. 21, 2019

Related U.S. Application Data

(60) Provisional application No. 62/449,404, filed on Jan. 23, 2017.

(51) Int. Cl.
*G01N 33/49* (2006.01)
*G01N 33/86* (2006.01)
(Continued)

(52) U.S. Cl.
CPC ......... *G01N 33/4905* (2013.01); *G01N 33/86* (2013.01); *G01N 21/272* (2013.01);
(Continued)

(58) Field of Classification Search
CPC ............... G01N 33/4905; G01N 33/86; G01N 2011/008; G01N 21/82
See application file for complete search history.

(56) References Cited

U.S. PATENT DOCUMENTS 4,879,432 A    11/1989   Vieillard
6,114,135 A    9/2000    Goldstein
(Continued)

FOREIGN PATENT DOCUMENTS

WO    2015038998 A1    3/2015

*Primary Examiner* — Paul M. West
(74) *Attorney, Agent, or Firm* — Davis, Brown, Koehn, Shors & Roberts, P.C.

(57) ABSTRACT

The disclosed apparatus, systems and methods relate to ATPA technology that provides a method for the real-time assessment of the polymerization of a sample, e.g., whole blood or blood plasma coagulation, by a non-contact acoustic tweezing device. The acoustic tweezing technology integrates photo-optical tests used in plasma coagulation assays with mechanical (viscoelastic) tests used in whole blood analysis. Its key disruptive features are the increased reliability and accuracy due to non-contact measurement, low sample volume requirement, relatively short procedure time (less than 10 minutes), and the ability to assess the level of Factor XIII function from measurements of the fibrin network formation time.

5 Claims, 11 Drawing Sheets

(51) Int. Cl.
    *G01N 21/27*    (2006.01)
    *G01N 21/82*    (2006.01)
    *G01N 21/17*    (2006.01)

(52) U.S. Cl.
    CPC ..... *G01N 21/82* (2013.01); *G01N 2021/1721* (2013.01); *G01N 2021/1725* (2013.01)

(56) References Cited

U.S. PATENT DOCUMENTS

| | | |
|---|---|---|
| 6,321,164 B1 | 11/2001 | Braun et al. |
| 2004/0147032 A1 | 7/2004 | Martin et al. |
| 2005/0230706 A1 | 10/2005 | Yagyu et al. |
| 2009/0130645 A1 | 5/2009 | Schubert et al. |
| 2013/0344519 A1 | 12/2013 | Leong et al. |
| 2014/0014509 A1 | 1/2014 | Yan et al. |

A

B

*Figure 7 (A) Tweezographs of EDTA-treated whole blood with added CaCl$_2$ and exposed to 0.9% saline (8 drops), tissue factor (TF) (8 drops) or cytochalasin D (8 drops). (B) Effect of TF on h at selected times. (C) Effect of cytochalasin D on h at selected times.*

APPARATUS, SYSTEMS AND METHODS FOR INTEGRATIVE PHOTO-OPTICAL/MECHANICAL TEST FOR NONCONTACT MEASUREMENT OF POLYMERIZATION

CROSS-REFERENCE TO RELATED APPLICATION(S)

This application claims the benefit under 35 U.S.C. § 371 to International PCT Patent Application No. PCT/US18/14879, filed on Jan. 1, 2018, which claims priority to U.S. Provisional Application No. 62/449,404 filed Jan. 23, 2017 and entitled "Integrative Photo-Optical/Mechanical Test for Noncontact Measurement of Polymerization," which is hereby incorporated by reference in its entirety under 35 U.S.C. § 119(e).

GOVERNMENT SUPPORT

This work was supported in part by grant number 1438537 awarded by the National Science Foundation. The government has certain rights in this invention.

TECHNICAL FIELD

The disclosed technology relates generally to noncontact methods, devices and systems for measuring polymerization of a sample.

BACKGROUND

The disclosure relates to apparatus, systems and methods for measuring polymerization of a sample, such as coagulation of blood or polymerization of another biological material.

Blood coagulation is the process in which the blood changes from a liquid to gel state in response to blood loss, referred to as the hemostatic process. The coagulation cascade is initiated by adhesion and activation of platelets at the injury site of the vessel wall and occurs through two separate pathways: the extrinsic and intrinsic, both converging on the common pathway. The extrinsic pathway is triggered by tissue factor (TF) in response to vascular trauma, and the intrinsic pathway is triggered by contact of the blood with dysfunctional endothelium or collagen. During the common pathway, fibrinogen is converted into fibrin by thrombin. The fibrin polymerization and its crosslinking by Factor XIII forms a blood clot. The hemostasis process is the result of a delicate balance between pro- and anti-coagulants, platelets and blood cells.

Due to a significant loss of blood during trauma or major surgery, patients often develop coagulopathy, i.e., a pathophysiological condition characterized by depletion of both pro- and anti-coagulants in blood. Coagulopathic patients are at high risks of both hemorrhage and thrombotic complications, which significant increase patient morbidity and mortality. The coagulation status of such patients could rapidly change from an anti- to pro-coagulant state during injury and resuscitation. Therefore, monitoring the coagulation status of coagulopathic patients, especially during blood transfusion or surgery is critical.

The devices currently available for rheological measurements induce contact with device walls or other artificial surfaces, which causes large measurement errors. Additionally, testing for coagulation parameters using available contact techniques requires a significant amount of time to obtain diagnostic data (at least 30 minutes) and a large sample volume (at least 0.4 milliliters).

Thus, there is a need in the art for fast and reliable noncontact devices, systems and methods that can work with low-volume samples.

BRIEF SUMMARY

Discussed herein are various devices, systems and methods relating to methods, systems and devices for the real-time assessment of whole blood or blood plasma coagulation by non-contact acoustic tweezing technology and for measuring polymerization characteristics of a sample, including but not limited to rheological measurements and polymerization kinetics.

No feature of the disclosed implementations is critical or essential unless it is expressly stated as being "critical" or "essential."

In one Example, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One Example includes a noncontact, acoustic-tweezing method of measuring time-dependent rheological and polymerization properties of a sample including: levitating the sample, modulating the amplitude of acoustic pressure applied to the sample so as to induce deformation, capturing at least one image of the sample, collecting at least one photo-optical measurement and at least one mechanical measurement from the captured images of the levitating sample during deformation, and determining at least one rheological property of the sample. Other embodiments of this Example include corresponding computer systems, apparatus, and computer programs recorded on one or more computer storage devices, each configured to perform the actions of the methods.

Implementations may include one or more of the following features. The method where the deformation is quasi-static or oscillatory. The method further including determining at least one kinetic property of sample polymerization. The method where the determined kinetic properties of sample polymerization are selected from the group including of: photo-optical tweezograph, mechanical tweezograph, reaction time, monomer formation rate, maximum monomer level, polymerization onset, polymerization rate, polymerization time, gel firmness and polymer network formation time. The method where the polymer network formation time is the time difference between the polymerization rate in a mechanical tweezograph and the monomer formation rate in a photo-optical tweezograph. The method where the rheological property is coagulation. The method where the at least one photo-optical measurement is selected from the group including of: light intensity, laser scattering intensity and turbidity. The method where the at least one mechanical measurement is elasticity. The method where the at least one image is photographic. The method where the at least one image is a laser scattering image. The method further including executing data analysis on the collected at least one photo-optical measurement and at least one mechanical measurement. The method where the sample is a biological material selected from the group including of: whole blood, blood plasma, mucus, sperm, lymph, synovial fluid, cerebrospinal fluid and soft biological tissue. The method where the sample is selected from the group including of: a polymer, a polymer gel and a polymeric liquid. The method where the at least one photo-optical measurement is selected from the group including of: average light intensity through central area of the sample and turbidity of the sample over time. The method where the one or more mechanical measurements are determined from quasi-static and oscillatory deformation of the sample for different acoustic pressure amplitudes at different times. The method where the one or more rheological property is selected from the group including of: elastic modulus, shear elasticity, shear viscosity, dynamic modulus, storage modulus, and loss modulus. The method where the fibrin network formation time (FNFT) is the time difference between the clotting rate (CR) in a mechanical tweezograph and the fibrin formation rate (FFR) in a photo-optical tweezograph. The method where the extracted coagulation kinetics data is selected from the group including of: photo-optical tweezograph, mechanical tweezograph, reaction time (RT), fibrin formation rate (FFR), maximum fibrin level (MFL), clot initiation time (CIT), clotting rate (CR), time to firm clot formation (TFCF), maximum clot firmness (MCF), and fibrin network formation time (FNFT). The method further including extracting coagulation kinetics data. The method further including evaluating functional levels of fibrinogen from at least one of RT, MFL, MCF, and FNFT data extracted from the photo-optical and mechanical tweezographs. The method further including evaluating functional levels of factor XIII. The method may also include from at least one of RT, MFL, MCF, and FNFT data extracted from the photo-optical and mechanical tweezographs. The method further including monitoring functional levels of fibrinogen or factor xiii to assess blood coagulation disorder. The method further including assessing the effects of a cross-linker from the determined polymerization kinetics. The method further including assessing the effects of cross-link breakers on the sample from the determined polymerization kinetics. The method further including assessing the effects of a cross-link inhibitors on the sample from the determined polymerization kinetics. Implementations of the described techniques may include hardware, a method or process, or computer software on a computer-accessible medium. The method further including extracting coagulation kinetics data. The method further including evaluating a functional level of fibrinogen. The method further including evaluating a functional level of Factor XIII. The method further including evaluating coagulation factor deficiency. The method may also include from at least one of RT, MFL, MCF, and FNFT data extracted from the photo-optical and mechanical tweezographs. The method further including monitoring functional levels of coagulation factors to assess blood coagulation disorder.

One Example includes a noncontact, acoustic-tweezing system for measuring time-dependent rheological and polymerization properties of a sample including: a levitator configured to levitate the sample, an amplitude modulator configured to modulate acoustic pressure applied to the sample so as to induce deformation, a camera configured to capture at least one image of the sample and generate captured images, and an analysis system configured to: collect: at least one photo-optical measurement of the sample and at least one mechanical measurement of the sample. The system also includes capturing images during deformation. The system also includes determining at least one rheological property of the sample.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

The following drawings form part of the present specification and are included to further demonstrate certain aspects of the disclosed ATPA methods, systems and devices. The disclosure may be better understood by reference to one or more of these drawings in combination with the description of specific embodiments presented herein.

FIG. 4A shows 0.90-mm radius drop of 3% gelatin at increasing times. FIG. 4B shows 0.90, 0.89 and 0.86 mm drops of 2%, 3% and 4% gelatin at 2 min. FIG. 4C plots location vs. aspect ratio curves of a 4% alginate drop with radius of 0.98 mm from 0 to 34 min.

In FIG. 11A, the deficient plasma is exposed to tissue factor (PT test). In FIG. 11B, the deficient plasma is exposed to ellagic acid

DETAILED DESCRIPTION

Figure 1A:
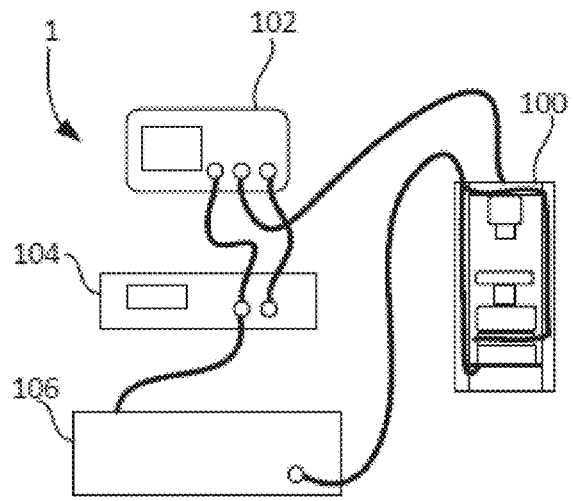
FIG. 1A depicts a schematic of the acoustic tweezing system, according to an exemplary embodiment.

The various embodiments disclosed or contemplated herein relate to a unique, integrated noncontact method for perioperative monitoring of whole blood or blood plasma coagulation. The disclosed systems, methods and devices relate to an acoustic tweezing polymerization analyzer (ATPA). The disclosed embodiments of the ATPA method, system and associated devices are referred to herein variously for brevity, including as the "ATPA method," though no specific modality is contemplated.

In various implementations, the disclosed ATPA method provides technology to measure the dynamics of polymerization in polymeric or biological fluids including the steps such as monomer production and cross-linked polymer network formation. In exemplary embodiments, the ATPA method integrates photo-optical measurements (such as light intensity or turbidity changes in the sample over time) with mechanical measurements (such as changes in bulk deformability of the sample over time), though each of the photo-optical and mechanical methods can be utilized without the other portion. In various implementations of the integrated ATPA method, these measurements are taken simultaneously using one single drop of sample fluid levitating or "tweezing" in air or an aqueous medium by acoustic radiation forces. Various implementations of the ATPA methods, systems and devices are disclosed herein. While much of this discussion focuses on blood, it is well understood that other samples of biological and other material are clearly contemplated and would be readily recognized by one of skill in the art.

Critical care patients such as trauma and major surgery patients often develop coagulopathy due to depletion of both pro- and anti-coagulants. They are at high risk of both bleeding and thrombotic complications and require monitoring of their coagulation status. The contact of a blood sample with artificial surfaces and its exposure to clot activators, which happen in all commercially available coagulation analyzers, may lead to improper assessment of blood coagulation and thus errors in predicting bleeding/thrombosis risks.

The levels of fibrinogen and Factor XIII in the blood correlate with the how and when blood coagulates. The lack of these factors leads to severe bleeding due to unstable clot structure and/or slow clotting. Therefore, a method of measuring these factors and monitoring of their functional levels is crucial for treatment of critical care patients and patients with coagulation disorders.

When applied to blood coagulation, the integrated photo-optical/mechanical method can measure the coagulation parameters of whole blood or blood plasma without exposing the blood sample to artificial reagents (ellagic acid, kaolin) or inducing sample contact with artificial surfaces. The method integrates "acoustic tweezing"-based photo-optical and mechanical tests to allow for accurate measurement of parameters of coagulation, including: reaction time (RT), fibrin formation rate (FFR), maximum fibrin level (MFL), clot initiation time (CIT), clotting rate (CR), time to firm clot formation (TFCT), maximum clot firmness (MCF), and fibrin network formation time (FNFT). The last parameter has not been measurable until the development of the presently disclosed ATPA method and associated systems and devices. Through these measurements, one can use the method to assess the functional levels of fibrinogen and Factor XIII in a blood sample, which are necessary for blood clot formation. When applied to other fluids, the method can detect the activity of molecules involved in the polymerization process or in the formation and cross-linking of fibrous proteins in biological tissues.

The integrated photo-optical and mechanical test is performed on the same sample drop during its levitation in the acoustic tweezing device. The data indicate that this integrated test provide the information about coagulation parameters (including the MCF) within 10 minutes (while current devices requiring at least 30 minutes) using the sample volume of just 4 microliters (~100 times less than the sample volume required in available coagulation analyzers).

In certain implementations, the system provides a method of measuring time-dependent rheological properties of a sample such as a biological sample, comprising several steps, none of which are essential. One step involves levitating the sample. Another step requires modulating the amplitude of acoustic pressure around the sample. Another step requires taking one or more images of the sample at different times. Another step requires taking one or more photo-optical measurements and one or more mechanical measurements from the one or more images. It would be apparent to one of skill in the art that certain of these steps may be performed in any order.

Another step requires determining the one or more rheological properties of the sample at different times from the one or more mechanical measurements. Another step requires assessing the polymerization kinetics from the one or more rheological properties and one or more photo-optical measurements. It will be appreciated by those of skill in the art that various additional steps may be performed, and that certain of these steps may be performed in any order and any number of times.

Various embodiments of the disclosed non-contact acoustic tweezing technology can be performed using the devices and methods disclosed in U.S. patent application Ser. No. 15/068,126 filed on Mar. 11, 2016, and Patent Cooperation Treaty Patent Application No. PCT/US2014/055559, filed on Sep. 15, 2014, both of which are entitled "Apparatus, Systems & Methods for Non-Contact Rheological Measurements of Biological Materials" and are incorporated by reference herein in their entireties.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the disclosed embodiments of the ATPA method.

EXPERIMENTAL TECHNIQUES & EXAMPLES

It is understood that in some embodiments the tweezograph is the graph of sample deformability ("mechanical tweezograph") or sample light intensity/turbidity ("photo-optical tweezograph") versus time. All kinetic data are determined from tweezographs.

In certain embodiments and Examples, "reaction time" refers to the onset of light intensity or turbidity change in a photo-optical tweezograph.

In certain embodiments and Examples, "polymerization onset" or "clot initiation time" is the onset of sample deformability change in a mechanical tweezograph.

In certain embodiments and Examples, "monomer formation rate" or "fibrin formation rate" is the time to reach the maximum rate light intensity or turbidity change in a photo-optical tweezograph.

In certain embodiments and Examples, "polymerization rate" or "clotting rate" is the maximum rate of sample deformability change in a mechanical tweezograph.

In certain embodiments and Examples, "polymerization time", "solidification time", or "time to firm clot formation" is the time it takes to reach a plateau in a mechanical tweezograph.

In certain embodiments and Examples, "maximum monomer level" or "maximum fibrin level" is the plateau value of light intensity or turbidity in a photo-optical tweezograph.

In certain embodiments and Examples, "gel firmness" or "maximum clot firmness" is the plateau value of the sample elasticity in a mechanical tweezograph.

In certain embodiments and Examples, "polymer network formation time" or "fibrin network formation time" is the time difference between reaching the "polymerization rate" or the CR in a mechanical tweezograph and the "monomer formation rate" or the FFR in a photo-optical tweezograph. The physical meaning of this parameter is the time delay between the processes of monomer formation and polymerization/clotting.

In certain embodiments and Examples, the sample may be whole blood, blood plasma, mucus, sperm, lymph, synovial fluid, cerebrospinal fluid, soft biological tissue or other known biological material, a polymer, a polymer gel, a polymeric liquid.

In certain embodiments and Examples, the functional level of fibrinogen is determined by integrating the RT, MFL, and MCF data from photo-optical and mechanical tweezographs. A higher fibrinogen level corresponds to a smaller RT, a higher MFL, and a higher MCF.

In certain embodiments and Examples, the functional level of a cross-linker (in case of polymerization) or Factor XIII (in case of coagulation) is determined from the FNFT data. It is understood that in these implementations, the lower the FNFT, the higher the functional level (activity) of a cross-linker or Factor XIII would be.

Blood Coagulation.

Blood coagulation is the process in which the blood changes from a liquid to gel state in response to blood loss, referred to as the hemostatic process. The coagulation cascade is initiated by adhesion and activation of platelets at the injury site of the vessel wall and occurs through two separate pathways: the extrinsic and intrinsic ones, both converging on the common pathway. The extrinsic pathway is triggered by tissue factor (TF) in response to vascular trauma, and the intrinsic pathway is triggered by contact of the blood with dysfunctional endothelium or collagen. During the common pathway, fibrinogen is converted into fibrin by thrombin. The fibrin polymerization and its crosslinking by Factor XIII forms a blood clot. The hemostasis process is the result of a delicate balance between pro- and anti-coagulants, platelets and blood cells. Due to a significant loss of blood during trauma or major surgery, patients often develop coagulopathy, a pathophysiological condition characterized by depletion of both pro- and anti-coagulants in blood. Coagulopathic patients are at high risks of both hemorrhage and thrombotic complications, which significant increase patient morbidity and mortality. The coagulation status of such patients could rapidly change from an anti- to pro-coagulant state during injury and resuscitation. Therefore, monitoring the coagulation status of coagulopathic patients, especially during blood transfusion or surgery is critical.

Measurement of Blood Coagulation.

Blood coagulation analysis is routinely performed to assess bleeding or thrombosis risks in surgical and critical care patients, patients on anticoagulant therapy, patients with chronic coagulation disorders such as coagulation factor deficiency, hemophilia and thrombophilia, and patients with other diseases that can impair the coagulation system (e.g., cancer, atherosclerosis, diabetes, and sickle cell disease). Two main approaches are currently used in this field. The first approach is photo-optical measurement of coagulation onset in blood plasma exposed to certain activators. Prothrombin Time/International Normalized Ratio (PT/INR), activated Partial Thromboplastic Time (aPTT), and Thrombin Time (TT) are all the result of such measurements. While each of these tests can measure different aspect of coagulation profile, they cannot provide a globe picture about hemostasis, even in combination. With the absence of platelet and red blood cells, the information yielded from these assays is further limited. The second approach, used in whole blood (global) coagulation analysis, is measurement of temporal changes in elasticity (stiffness or firmness) of coagulating blood. Whole blood coagulation tests are typically presented in a graphical form, as cigar-like traces overlaid with a reference curve. Numeric data (clot initiation time, coagulation rate, maximum clot firmness and the like), extracted from traces, are also provided to clinicians for proper diagnosis.

Mechanical Measurement of Blood Coagulation.

Contact "pin-and-cup" methods such as thromboelastography (TEG) and rotational thromboelastometry (ROTEM) are currently available to measure the coagulation status of whole blood. These methods measure temporal changes in the shear force between a disposable cup containing a 0.3-0.4 ml sample of whole blood and a pin immersed in the blood sample. Intrinsic pathway activators such as kaolin or ellagic acid are required to initiate coagulation using this approach. The "pin-and-cup" techniques accurately diagnose hyperfibrinolysis and are helpful but not reliable tools in screening for hypercoagulable states and transfusion guidance. However, the contact of a blood sample with the pin and cup surfaces creates artificial conditions for blood coagulation, leading to substantial differences from the dynamics of hemostasis in the body. This inherent deficiency is an important reason behind poor standardization and high variability of these methods, their inability to determine disorders of primary hemostasis, unreliability in detection of impaired platelet function and prediction of bleeding after major surgery, insensitivity to warfarin effects and a strong effect of heparin flush on thromboelastographic parameters leading to the necessity of discarding a large volume of blood before measurement. Previous studies also indicated that the shear stress applied to blood sample has exceed the linear region of sample elasticity which has been showed to interfere clot formation process and limit the sensitivity and speed of measurements. Even with intrinsic pathway activators present, the coagulation process occurring in "pin-and-cup" devices remain slow. A significant amount of time (30-60 minutes) is required to obtain the results needed for diagnosis unless the extrinsic pathway activators (e.g., tissue factor) are used.

Acoustic Levitation.

Drops, bubbles, solid particles, and other objects exposed to an acoustic wave field experience acoustic radiation pressure. In the case of intense standing waves, the radiation pressure is significant and can balance the gravitational force, levitating the object at a certain spatial position. In the past few decades, several acoustic levitation-based methods have been employed to measure the mechanical properties of fluid samples, often with complex surface properties. In these methods, the hydrodynamic theory and perturbation analysis were applied to infer some of the material constants from experimental data on quadrupole shape oscillations of the samples.

Non-Contact Rheology System.

Figure 1B:
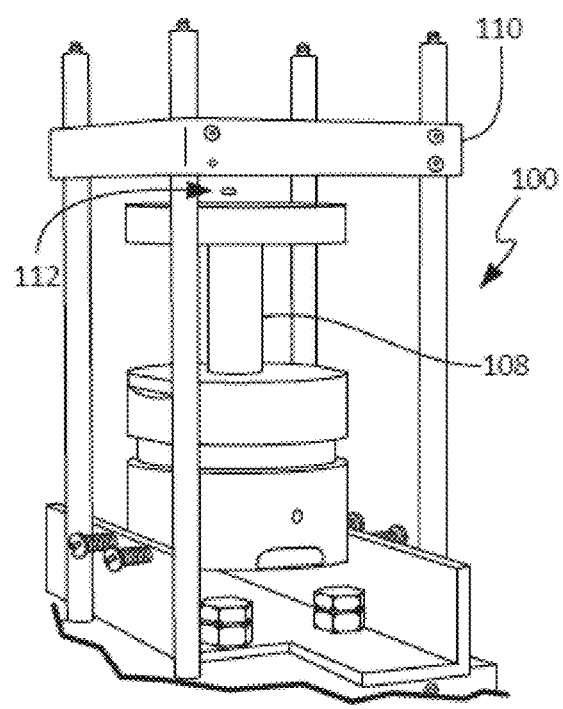
FIG. 1B depicts a perspective view of the an exemplary levitator of the acoustic tweezing system, according to one embodiment.
Figure 1C:
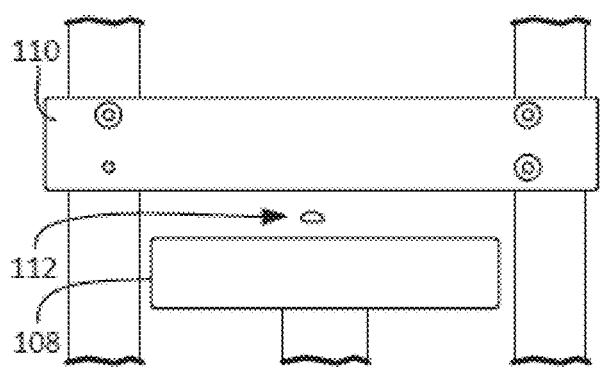
FIG. 1C depicts a close-up side view of a levitating sample, according to the embodiment of FIG. 1B.
Figure 1D:
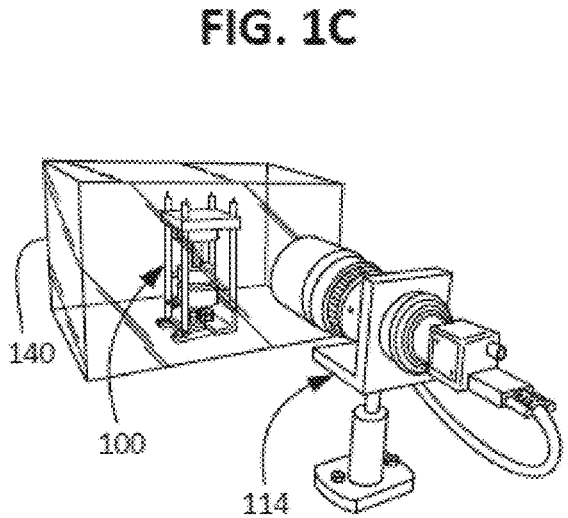
FIG. 1D depicts a perspective view of a camera, according to an exemplary embodiment.
Figure 1E:
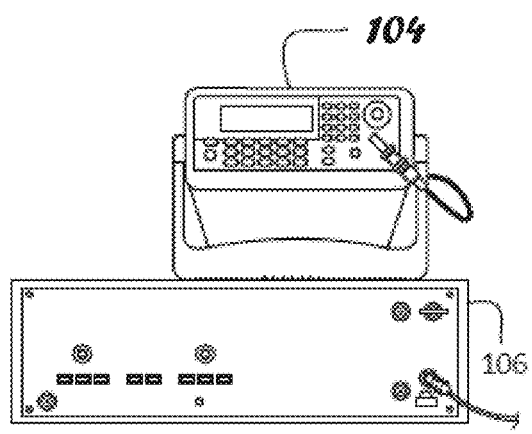
FIG. 1E depicts front view of the function generator and amplifier, according to an exemplary embodiment.

According to one implementation, a system for levitating the sample, which can be a biological sample, is provided. One previously-disclosed exemplary implementation of such an acoustic tweezing system 1 and associated components are depicted in FIGS. 1A-1E. FIG. 1A depicts a schematic overview of the acoustic tweezing system 1, comprising a levitator 100 that is in operational communication with an oscilloscope 102, a function generator 104, and an amplifier 106. As is shown in FIG. 1B, in exemplary embodiments of the acoustic tweezing system 1, the levitator comprises a transducer 108, such as an acoustic transducer 108 and reflector 110. FIG. 1C shows a detailed depiction of a sample 112 being levitated according to this embodiment. As is shown in FIG. 1D, in exemplary embodiments, the acoustic tweezing system 1 further comprises a camera 114 and an environmental control chamber. A further implementation of the levitator 100 comprising the function generator 104 and an amplifier 106 is further shown in FIG. 1E.

Figure 2:
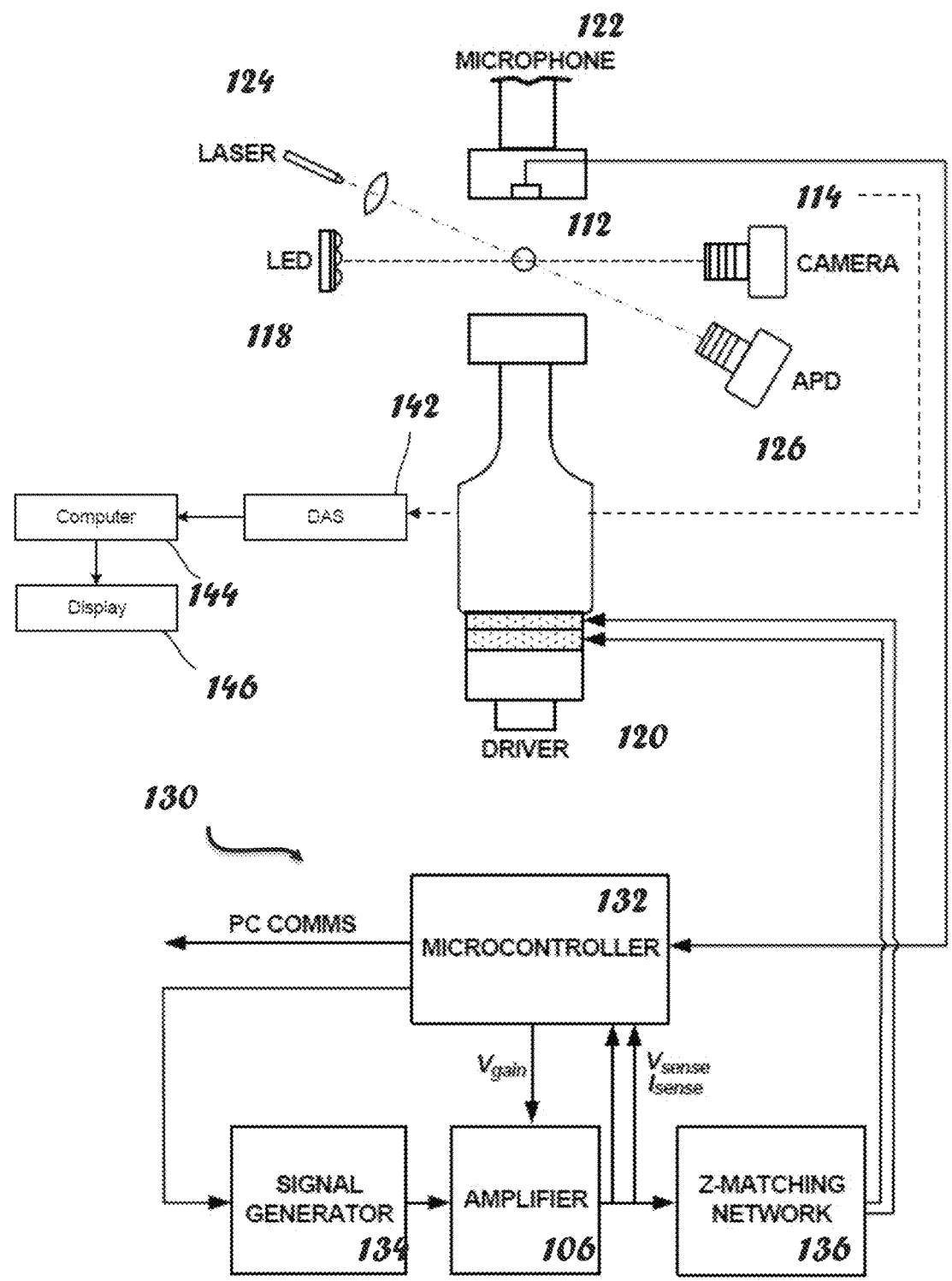
FIG. 2 is a schematic diagram of the acoustic tweezing system, according to a further embodiment.

A further implementation of the acoustic tweezing system 1 is depicted in the implementation of FIG. 2. In this implementation, the sample 112 is levitated above a driver 120 and below a microphone 122, wherein images can be captured via a camera 114 illuminated by a light source 118, such as an LED 118.

In this implementation, the system 1 comprises a laser 124 and diode 126 such as an avalanche photodiode (APD) 126 for the capture and measurement of transmitted or scattered photo-optical signal at a defined wavelength range, therefore being configured to measure various optical properties of the levitated sample 112.

Further, in the implementation of FIG. 2, the driver 120 and microphone 122 are in operable communication with an operations system 130. In this implementation of the operations system 130, a microcontroller 132, signal generator 134, amplifier 106 and Z-matching network 136 are provided, such that an input signal can be generated and amplified before being sent to the transducer 108 resulting in the radiation vibration of the driver 120.

It is understood that by placing a reflector at a specified distance from the transducer surface (either a full or half wavelength apart), the acoustic tweezing system 1 generates a standing wave field with pressure node and antinode with minimum and maximum pressure, respectively. The acoustic radiation pressure applied on the surface of the drop is able to levitate objects between the node and antinode, where the resulting acoustic radiation force balances gravity.

In use, according to certain implementations, a small drop of blood or other biological fluid 112 will be dripped into the opening 116, where it will be levitated in a standing acoustic wave field 150 and forced into shape oscillation. The sample 112 is levitated above a driver 120 and below a microphone 122, wherein images can be captured via a camera 114 illuminated by a uniform soft light source 118, such as an LED 118. Greyscale images can be recorded at different frame per second (FPS) depending on the requirements of the experiment or implementation and stored in the data acquisition system through a communications system such as a high speed USB 3.0 cable, wireless transmission or the like for further shape deformation and/or photo-optical properties analysis by customized MATLAB program via a data acquisition system 142.

Certain implementations feature at least one data acquisition system 142, which may include the oscilloscope and amplifier (depicted in FIG. 1A), and other means of data acquisition and transmission as would be apparent to one of skill in the art. The shape deformation of the sample will be recorded using an optical camera 114 and analyzed on a computer 144 using theoretical and computational models. The rheological data are displayed on a monitor 146. Further implementations may comprise a pressure control system, a pressure vessel and/or housing, though these components are not essential.

The driver or transducer consists of two 3.175-mm thick piezoelectric discs (Channel Industries, Santa Barbara, Calif.) and homemade aluminum bottom mass and horn to amplify and concentrate the radiation pressure. The working frequency of this transducer is nominally 30 kHz, requiring slight retuning to compensate for temperature shifts. The transducer and the reflector (an aluminum cylinder) were mounted either a full or half wavelength apart, and the assembly could be optionally inserted into a custom fabricated and sealed environmental chamber for pressure, temperature and humidity control or a 3-D positioning system custom built using parts bought from Thorlabs (Newton, N.J.). The 30 kHz sinusoidal input signal was generated by a function synthesizer (Agilent 33220A, Santa Clara, Calif.) and amplified (Krohn-Hite 7500, Brockton, Mass.) before being sent to the transducer, whose resulting vibration creates an acoustic standing wave in the air gap between the transducer and the reflector.

Modulating Amplitude of Acoustic Pressure.

Various implementations require the variation of the acoustic pressure amplitude (often called a pressure sweep) in order to induce sample deformation. This step is accomplished by a way of a "mechanical" intervention, such as by varying the amplifier input voltage at a fixed frequency, or by varying the frequency at a fixed voltage input. The pressure sweep is completed in 30 s or less, which is much shorter than the blood clotting time.

Measurement of Whole Blood or Blood Plasma Coagulation.

Microliter drops of whole blood collected from healthy volunteers or commercial control plasma were levitated in air by acoustic radiation forces using the disclosed acoustic tweezing device. The coagulation kinetics of the blood or plasma, including reaction time (RT), fibrin formation rate (FFR), maximum fibrin level (MFL), clot initiation time (CIT), clotting rate (CR), time to firm clot formation (TFCT), maximum clot firmness (MCF), and fibrin network formation time (FNFT) were assessed from photo-optical (light intensity) and mechanical (drop shape) data. FNFT was determined as the time difference to reach the CR and FFR in mechanical and photo-optical tweezographs, respectively.

Measurement of Blood Coagulation in the Presence of Activators and Inhibitors.

Whole blood and blood plasma samples were exposed to pro-coagulants/coagulation activators (tissue factor, fibrinogen) and coagulation inhibitors including antiplatelet agent Cytochalasin D and anti-thrombotic agent GPRP during levitation in the disclosed acoustic tweezing device. Changes in the coagulation status between different experimental groups were detected within 10 minutes. Similarly, less than 7 minutes was required to detect significant changes in RT, CIT, and MCF between blood plasma samples exposed or not to coagulation activators or inhibitors.

Image Collection.

Figure 3:
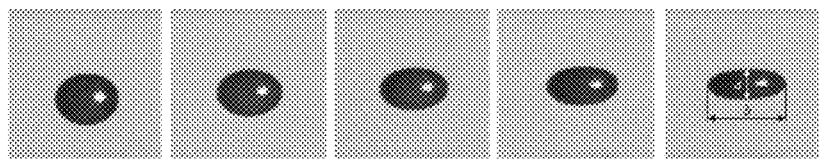
FIG. 3A depicts a sequence of photos of a drop of whole blood under quasi-static acoustic tweezing.
FIG. 3B is a mechanical tweezograph of 47 drops of citrated whole blood undergoing coagulation initiated by $CaCl_2$.
Figure 3:
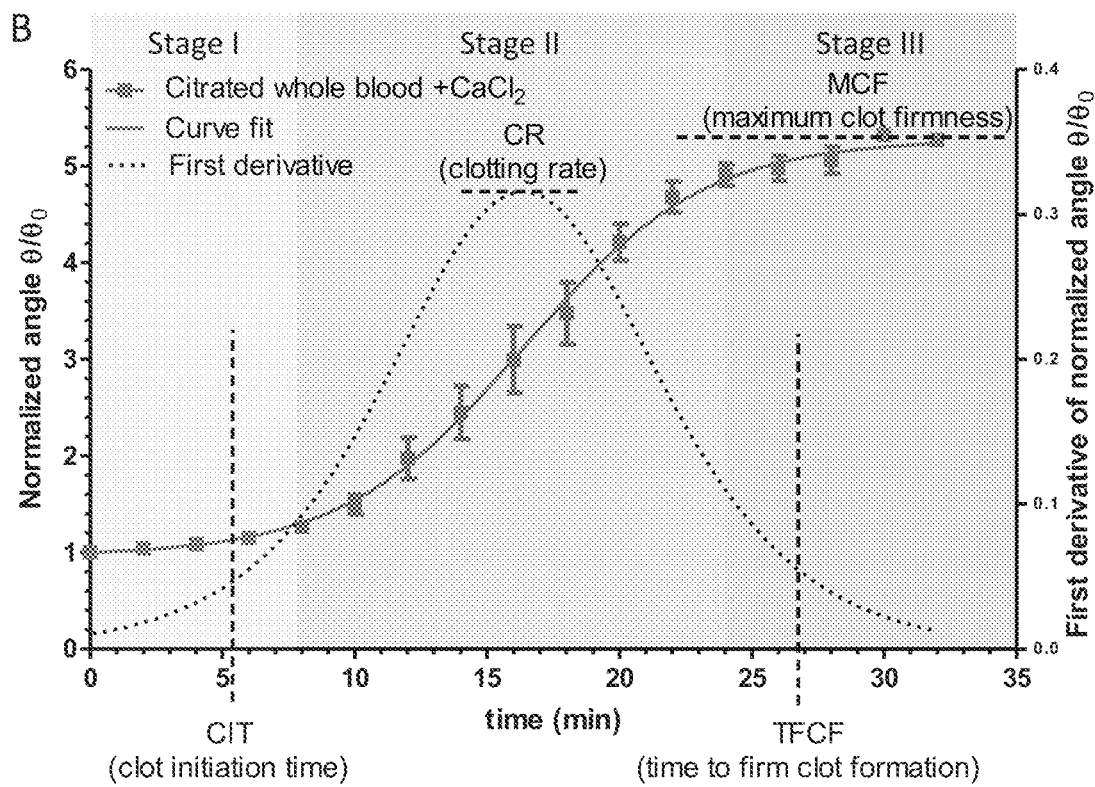
Figure 4:
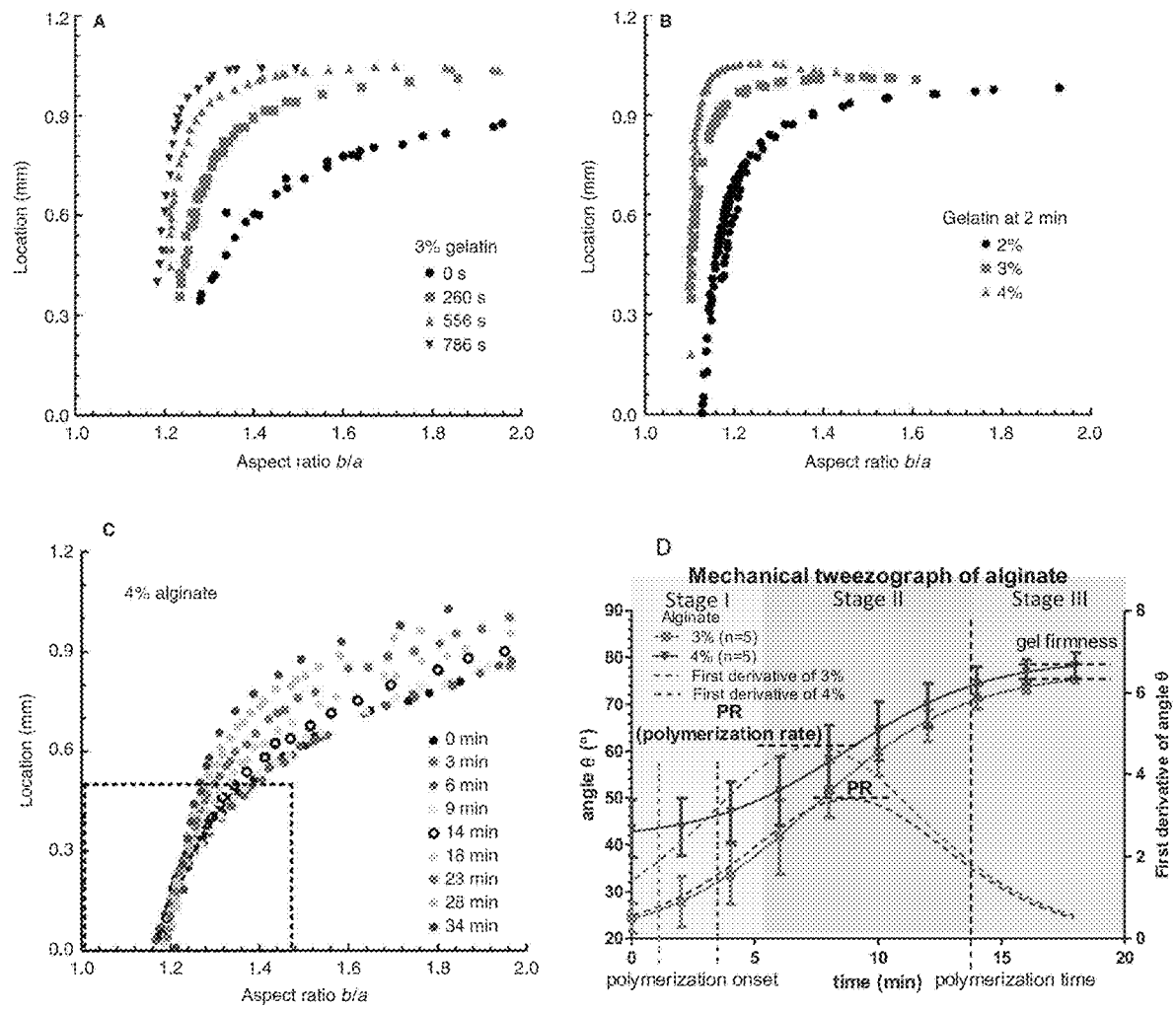
FIGS. 4A-4C depict raw mechanical data (location vs. aspect ratio) for porcine gelatin and alginate samples obtained by increasing and decreasing pressure amplitude.
FIG. 4D is a mechanical tweezograph ($\theta$ vs. time) of 5 drops of 3% alginate and 5 drops of 4% alginate for 18 min of tweezing. Nominal radii of drops are 0.98 mm, on average.
Figure 5:
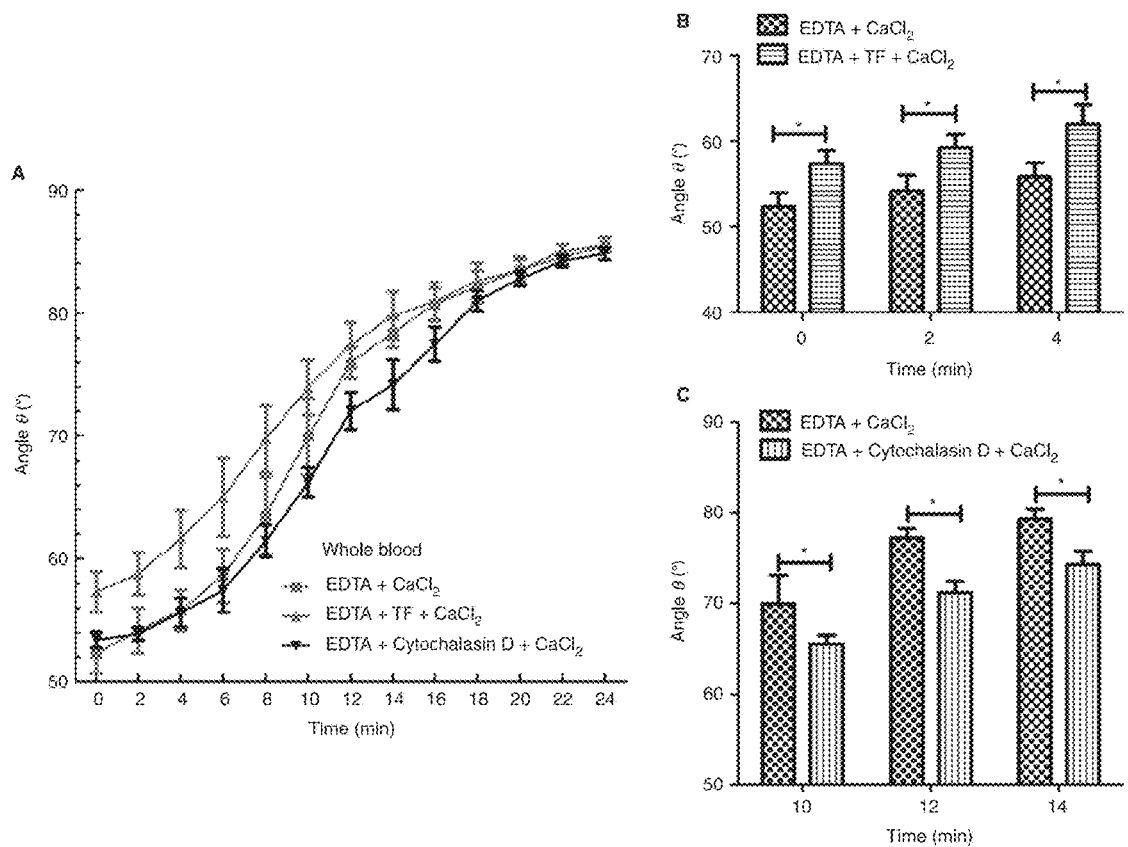
FIG. 5A depicts mechanical tweezographs of EDTA-treated whole blood with added $CaCl_2$ and exposed to 0.9% saline (8 drops), tissue factor (TF) (8 drops) or cytochalasin D (8 drops).
FIG. 5B depicts the effect of TF on $\theta$ at selected times.
FIG. 5C depicts the effect of cytochalasin D on $\theta$ at selected times.
Figure 6:
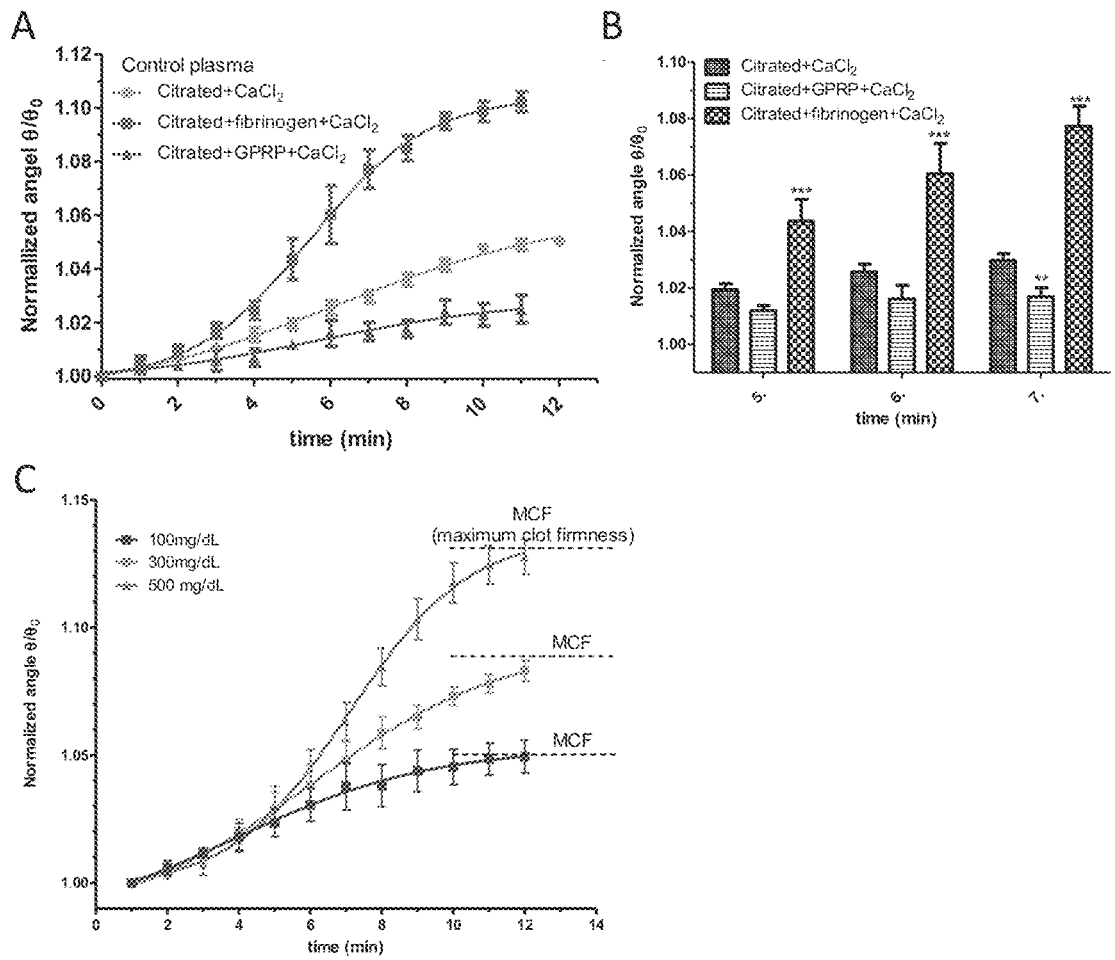
FIG. 6A depicts mechanical tweezographs of citrated control plasma with added $CaCl_2$, exposed to 0.9% saline (9 drops), Fibrinogen (9 drops), or GPRP (9 drops).
FIG. 6B depicts the effect of Fibrinogen and GPRP on slope angle $\theta$ at 5, 6, and 7 minutes. $p<0.01$, *$p<0.001$.
FIG. 6C depicts mechanical tweezographs of plasma with fibrinogen levels of 100, 300, and 500 mg/dL indicating an increase in MCF with fibrinogen concentration.

Another step requires taking one or more images of the sample by a camera at different times, as is discussed below in relation to the Examples surrounding FIGS. 3A-3B.

Photo-Optical and Mechanical Measurements.

Another step requires taking one or more photo-optical measurements and one or more mechanical measurements from the one or more images, as is shown below in relation to the Examples surrounding FIGS. 3-10.

Evaluation of Rheological Properties.

Another step requires determining the one or more rheological properties of the sample at different times from the one or more mechanical measurements, as is discussed below in relation to the Examples surrounding FIGS. 3-6.

Assessing Polymerization Kinetics.

Figure 10:
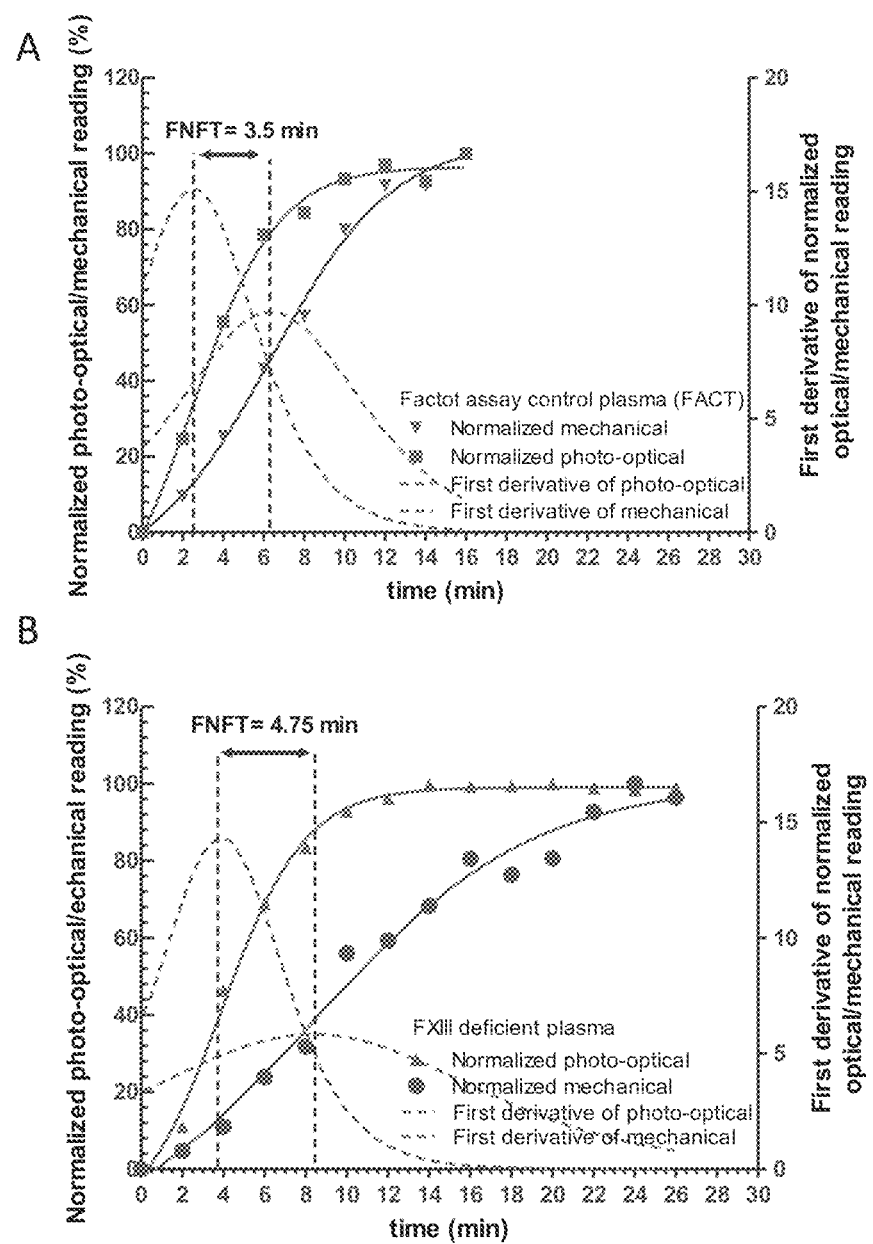
FIG. 10A depicts the combined photo-optical and mechanical tweezographs of normal plasma (FACT), indicating that the fibrin network formation time (FNFT) is 3.5 minutes.
FIG. 10B depicts the combined photo-optical and mechanical tweezographs of Factor XIII deficient plasma, indicating the FNFT is 4.75 minutes.

Another step requires assessing the polymerization kinetics from the one or more rheological properties and one or more photo-optical measurements as discussed below in relation to the Examples surrounding FIG. 10.

EXAMPLES

The following Examples are put forth so as to provide those of ordinary skill in the art with a complete disclosure and description of how the articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Further representative Examples are provided herein.

Example 1: Quasi-Static Acoustic Tweezing

Quasi-Static Experimental Procedure.

Samples (~4 µL nominally) were deployed manually into a pressure minimum of the standing wave using a gastight 100 µL glass syringe (Hamilton 7656, Reno, Nev.) with a polytetrafluoroethylene-coated stainless steel blunt-tipped needle (Hamilton 8646).

In an implementation of a quasi-static experiment, the input is fixed at 400 mV, with frequency starting around 29.5 kHz, which is always lower than the resonant frequency. In these implementations, sample deformation is induced by increasing the standing wave pressure amplitude. This is accomplished by slowly tune up frequency towards the resonant frequency. In the beginning of the experiment, according to this implementation, a sample drop is injected into the pressure field by syringe, an increased pressure is applied to trap the sample in the central area while pulling out the syringe. After the drop is levitated, the pressure will be decreased to an aspect ratio of about 1.2, which can be referred as "resting status," to maintain stable status with minimum pressure on bulk surface.

To induce deformation, slowly tuning frequency toward to resonant frequency will increase the pressure level in the field therefore raising the aspect ratio to about 1.5 and pushing the drop towards the pressure node location. This compression process normally takes about 10 to 15 seconds and the information of vertical location and drop shape deformation is obtained by an acA1920-25 um camera (Basler, Ahrensburg, Germany) at 4 FPS. After compression, pressure is reduced to "resting status" for holding until the next compression. In one representative example, the interval between compressions can be about 1-3 minutes, though it is understood that the duration, as with all of the above described steps, can depend on the implementation. The spatial resolution of the images can be, for example, 0.012 mm, as they were in one assessed implementation.

FIG. 3A shows representative shapes of a whole blood sample undergoing an acoustic tweezing experiment according to one implementation. As the quasi-static technique relies on the fact that, as the acoustic pressure amplitude changes (pressure sweep), the location and deformation of a sample drop are uniquely determined by its rheological properties and size as seen in this FIG. 3A, an increase in the deformation of the sample correlates with an increase in its vertical position. It is understood that with an increase in pressure (photos from left to right), the drop center lifts up and the drop experiences higher deformation.

FIG. 3B is a mechanical tweezograph of citrated whole blood undergoes coagulation cascade, initiated by $CaCl_2$ solution. The slope of the initial portion of a location vs aspect ratio curve (which is an effective stress/strain curve) shown in FIG. 3B represents elasticity or stiffness of the sample. It is understood that at least four kinetic parameters can be measured from the mechanical tweezograph: clot initiation time (CIT), time to firm clot formation (TFCF), clotting rate (CR), and maximum clot firmness (MCF).

Example 2: Quantification of Drop Size, Deformation and Location

Location and shape deformation of tweezing samples were obtained by analyzing the image sequences using a custom program written in MATLAB (Mathworks, Natick, Mass.) which relied on the MATLAB image processing toolbox. The analysis began with edge detection using a modified Canny method, as has been previously described. The "blob analysis" tools within MATLAB were then used to find the centroid of the drop and quantify deformation as an aspect ratio (width b/height a, cf. FIG. 3A). Location was measured as a vertical distance from the sample centroid to a fixed location on the apparatus. This Example plots location, a measure of the acoustic stress applied to the drop to lift it, as a function of aspect ratio, a measure of the strain resulting from the applied acoustic stress (FIG. 3B). The effective stress/strain curve shape begins at low aspect ratio, where the location increases approximately linearly with aspect ratio until the gel drop begins to yield, and thereafter the drop deforms more readily than its location increases. Slopes of the initial portion of location vs aspect ratio curves were obtained by linear regression, and quantified by calculating the angle of inclination to the horizontal (aspect ratio) axis. Hence, for a line of slope m, reference is made to an angle $\theta=\arctan(m)$. For convenience, the slope angle vs. time curves are referred to herein as "tweezographs."

Example 3: Application of the Quasi-Static Acoustic Tweezing Method to Biological Polymers to Measure the Changes in Rheological Properties When gelatin or alginate are diluted in water, they form hydrogels characterized by much higher bulk elasticity that the initial solutions of these polymers. FIGS. 3A-3B and 4A-4D demonstrate that quasi-static deformation tests can capture changes in the sample elasticity during gelation of those proteins.

Methods.

In one Example, two gel mixtures were used: 300-bloom gelatin from porcine skin (Sigma-Aldrich) and sodium alginate (Sigma Aldrich). Gel solutions were prepared by hydrating gelatin or sodium alginate in distilled water for ten minutes, then adding boiling distilled water to achieve the desired concentration. Calcium carbonate $CaCO_3$ (Sigma-Aldrich) in combination with 6% (w/w) D-(+)-Gluconic acid δ-lactone (GDL, Sigma-Aldrich) was used as a source of calcium ions to initiate gelation of sodium alginate. The molar ratio of a basic calcium ion to carboxyl was kept at 0.36. The sodium alginate solution was mixed and vortexed with the $CaCO_3$ suspension for one minute. A fresh aqueous GDL solution was then added to the resulting mixture to initiate gelation by increasing the pH value therefore increase the solubility of $CaCO_3$. The samples were levitated and quasi-static acoustic tweezing was performed to measure the changes in rheological properties. The statistical data were presented as mean±standard error of the mean (SEM). Statistically significant differences were set at $p<0.05$ (95% confidence).

Results:

The location vs. aspect ratio curves plotted in FIGS. 4A-4D depict the location compared to the aspect ratio for porcine gelatin and alginate samples obtained by increasing and decreasing pressure amplitude. This Example and FIGS. 4A-4D demonstrate that quasi-static acoustic tweezing is sensitive to changes in bulk elasticity occurring during gelation process. For both gelatin and alginate, the sample location increases approximately linearly with aspect ratio until breaching the gravity-controlled limit. Beyond this limit, the drop deforms more readily without much changes in its location. In the linear regime, the slope of the location vs. aspect ratio curve for gelatin increases with time until 13 min later, when the sample is fully gelled, as is shown in FIG. 4A.

FIG. 4B shows the concentration dependence of gelatin drops at 2 min into an experiment, when they are partially gelled. The slope in the linear region of the location vs. aspect ratio curves increases with increasing gelatin concentration.

For alginate, the gelation process will only start after exposure to calcium ions. Accordingly, a GDL solution was used to initiate alginate gelation in this Example. FIG. 4C shows the full stress/strain curves at selected times up to 28 minutes. The box indicates the portion of the data for which linear regression was performed for location vs. aspect ratio to obtain h. The linear response region is restricted to the data in the bounding box in the lower left corner of FIG. 4C.

Mechanical Tweezograph.

As shown in FIG. 4D, after performing linear regression on the data in the box, the mechanical tweezograph is obtained, which plots the linear slope angle θ vs. time. The mechanical tweezograph shows that, as with the gels, the higher concentration is always stiffer. It is understood that at least four kinetic parameters can be measured from this tweezograph: polymerization onset, polymerization rate (PR), polymerization time and gel firmness. Those of skill in the art will appreciate other possible implementations.

Additionally, the elastic modulus (firmness), as quantified by angle θ, dramatically increases for 4% alginate at about 4 minutes after the alginate droplet injection into the levitator. After about 14 minutes, θ begins to level off with increasing time, indicating the approach to the fully gelled state. For this Example, these three distinct regions as Stage I (initial gelation or coagulation), Stage II (rapid gelation or coagulation), and Stage III (convergence to fully gelled or coagulated) in FIG. 4D. Taken together, FIG. 4 confirms that in this Example and other related implementations, it is possible to take θ as a measure of the sample elastic modulus, and the method itself is capable of measuring time dependent changes in the elastic modulus of reacting samples.

Examples 4-6 show application of the quasi-static acoustic tweezing method to whole blood samples from human subjects with different heathy conditions to assess their whole blood coagulation status.

Example 4: Application of the ATPA Method to Healthy Volunteer Whole Blood Samples and Identification of the Normal Ranges of Coagulation Parameters Like the previously described gelation process implementations, the blood coagulation implementations involve fibrin polymerization and cross-linking, leading to the formation of a blood clot: a fibrin network with embedded red blood cells and platelets. It is understood that the blood clot—and its major constituents—demonstrate viscoelastic behavior. Previous studies have demonstrated that fibrinogen is cleaved into fibrin early in the coagulation process, and then Factor XIII cross-links fibrin, thus stabilizing the blood clot and increasing its elasticity (firmness). Therefore, for blood coagulation analysis, it is essential to have a technique which is highly sensitive to elasticity change.

During this clotting process, the elasticity of the blood sample increases until reaching a plateau, where the clot behaves as a purely elastic material. In these examples, the elastic modulus of the blood drop starts increasing at a certain time point (referred to as "clot initiation time") and reaches its maximum level ("maximum clot firmness") at the time point referred to as "time to firm clot formation". Most experimental studies on clot viscoelasticity were done with fibrinogen solutions, but not with whole blood.

In this Example, 25 volunteers' data were analyzed for the results reported in FIG. 3B. 12-15 volunteers' blood were subject to TF and Cytochalasin D, as reported in FIGS. 5A-5C. The results were evaluated with t-test and one-way ANOVA using GraphPad Prism (GraphPad Software, La Jolla, Calif.). The statistical data were presented as mean±standard error of the mean (SEM). Statistically significant differences were set at $p<0.05$ (95% confidence).

The mechanical tweezograph of citrated whole blood (FIG. 3B) shows three stages of blood elasticity increase, similar to what observed during hydrogel gelation (FIG. 4D). At short times (Stage I), normalized angle ($\theta/\theta_0$) increases gradually as coagulation proceeds. Following this initial mild increase in firmness (Stage I), there follows a period of rapid increase (Stage II) in $\theta/\theta_0$. This period of rapid increase in firmness is then followed by its leveling off (Stage III). It is noteworthy that the coagulation process converges at long times to roughly the same Stage III path, with normalized angle reaching MCF value of 5.27±0.16 (mean±SEM) at about 32 minutes.

FIGS. 5A-5C demonstrate that the disclosed ATPA method is able to identify the impact of TF and Cytochalasin D on whole blood coagulation process. FIG. 5A depicts mechanical tweezographs of EDTA-treated whole blood with added $CaCl_2$ and exposed to 0.9% saline (8 drops), tissue factor (TF) (8 drops) or cytochalasin D (8 drops). All three groups had similar MCF. FIG. 5B depicts the effect of TF on $\theta$ at selected times. Samples treated with TF are immediately stiffer compared to untreated group. FIG. 5C depicts the effect of cytochalasin D on $\theta$ at selected times. Samples treated with cytochalasin D remain less stiff compared to untreated group through 14 minutes.

In this Example, samples treated with TF are immediately stiffer (TF: initial $\theta$=57.3±1.63°, untreated: 52.32±1.64°) and, because they show almost immediate Stage II rapid growth in firmness and continue to be stiffer than the untreated group throughout the untreated group's Stage I and II coagulation, as seen in FIG. 5B. On the other hand, samples treated with Cytochalasin D (FIG. 5C). display a longer Stage I with a delayed onset of Stage II, and thus remain less stiff relative to the untreated group. By 25 min, both treated and untreated samples converge to a similar Stage III firmness (mean±SEM: untreated, 85.46±0.27°; TF, 85.51±0.60°; Cytochalasin D, 84.79±0.49°).

Example 5: Application of the ATPA Method to Commercial Control Plasma Samples and the Effects of Pro- and Anti-Thrombotic Agents on Blood Plasma Coagulation To establish that the ATPA method has the ability to identify abnormal coagulation status, commercial blood plasma (FACT) samples were exposed to pro- or anti-thrombotic agents (fibrinogen and Gly-Pro-Arg-Pro (GPRP). Low levels of fibrinogen in plasma are associated with weak clot strength leading to an increased risk of bleeding. However, high fibrinogen concentration in plasma may increase a risk of thrombosis. The accurate and timely measurement of functional fibrinogen levels is important. GPRP is a strong inhibitor of fibrin polymerization by blocking the y chains of the fibrinogen molecule. Increasing concentrations of GPRP is expected to have a distinctive inhibition effect on coagulation process.

Methods.

Factor assay control (FACT) plasma, which is blood plasma pooled from 30 or more healthy human donors, was purchased from George King Bio-Medical (Overland Park, Kans.). Low fibrinogen control plasma with concentration of 100 mg/dL was purchased from Fisher Scientific (Hampton, N.H.). A high fibrinogen solution with concentration of 4000 mg/dL was prepared as stock solution. Three different concentrations of fibrinogen (100, 300, and 500 mg/dL) in blood plasma were tested. GPRP was diluted in PBS at 100 mmol/L as stock solution. The final concentration of GPRP in blood plasma was 2, 4, or 8 mmol/L. The linear regression analysis of the photo-optical and mechanical tweezographs was done using GraphPad Prism to determine the values of RT, MFL, and MCF at different fibrinogen and GPRP concentrations. The results were evaluated with one-way ANOVA using GraphPad Prism. The statistical data were presented as mean±standard error of the mean (SEM). Statistically significant differences were set at $p<0.05$ (95% confidence).

Results.

The mechanical tweezograph of FACT plasma depicted in FIGS. 6A-6C shows a three-stage increase in elasticity, similar to what was observed for whole blood. As shown in FIG. 6A, high fibrinogen plasma produces much stiffer clots ($\theta/\theta_0$=1.10) than FACT ($\theta/\theta_0$=1.05) or GPRP-treated plasma ($\theta/\theta_0$=1.02). According to FIG. 6B, a significant difference in clot firmness between high fibrinogen plasma and FACT was already observed at 5 minutes of sample tweezing (FACT: $\theta/\theta_0$=1.02±0.002, high fibrinogen: 1.04±0.01), while GPRP-treated plasma showed a significant decrease in clot firmness as compared to FACT starting at 7 minutes (FACT: 1.03±0.002, GPRP: 1.02±0.003).

According to FIG. 6C, a change in fibrinogen concentration has no effect on sample elasticity during Stage I (first 5 minutes of measurement). Maximum clot firmness (MCF) of each group can be identified. However, the effect of fibrinogen on blood plasma becomes pronounced at Stage II, leading to different MCF values: 1.059±0.0003 at 100 mg/dL, 1.085±0.0030 at 300 mg/dL, and 1.112±0.0051 at 500 mg/dL. In this Example, it was possible to find a good correlation ($R^2$=0.90) between fibrinogen concentration and MCF, indicating that the ATPA can reliably measure the fibrinogen concentration in blood plasma.

Example 6: Application of the ATPA Method to Tobacco Products Consuming Subjects and Identification of the Impact of Tobacco Products on Whole Blood Coagulation Previous studies have suggested that smoking could raise epinephrine in plasma, thus leading to the high concentration of fibrinogen and thrombin in the circulating system. Smoking was also found to increase platelet activation, which disturbs the hemostatic equilibrium, accelerates the coagulation, and leads to a pro-coagulated state. Scanning electron microscopy was used to document the fibrin polymer formation after smoking—this study showed a significantly thinner, denser fibers within the clot matrix, and an increased activity of Factor XIII, leading to stronger clots.

Methods.

Whole blood was collected into Vacutainers with EDTA and sodium citrate via venipuncture from heathy non-smoking and smoking volunteers. The ATPA test, together with standard coagulation assays, was performed to assess volunteers' coagulation status. Within 4 hours after blood collection, half of the blood samples will be centrifuged to collect platelet poor plasma (PPP), the rest of samples were re-calcified by mixing with calcium chloride solution, as done previously. By applying the quasi-static acoustic tweezing technique to a blood drop, the ATPA parameters such as CIT, CR, TFCF, MCF were measured and compared between smokers and non-smoking individuals. The results were evaluated with one-way or two-way ANOVA using GraphPad Prism. The statistical data are presented as mean±standard error of the mean (SEM). Statistically significant differences were set at $p<0.05$ (95% confidence).

Both whole blood and blood plasma samples from smokers have shorter CIT and TFCF and higher CR and MCF than samples from non-smoking subjects.

Examples 7-10 establish the application of the ATPA method to the measurement of functional levels of coagulation factors in blood plasma: development of light intensity (optical density) reading of blood plasma and integration of photo-optical and mechanical data for measurement of the coagulation process.

Example 7: Development of Photo-Optical Tweezographs for the Measurement of Coagulation in Blood Plasma Samples Traditionally, the coagulation status of patients is routinely measured by using platelet poor plasma (PPP) exposed to coagulation activators such as tissue factor (TF) or ellagic acid, which trigger the extrinsic and intrinsic pathways of coagulation, respectively. The assessment of prothrombin time (PT) and the associated international normalized ratio (INR) in TF-exposed plasma or active thromboplastin time (aPTT) in ellagic acid-exposed plasma was performed based on light intensity reading. Specifically, the PT and aPTT values were defined as the reaction time (RT) of TF- and ellagic acid-exposed plasma, respectively. Accordingly, the ATPA system and method provides a non-contact environment for coagulation measurement of blood plasma using photo-optical data.

Photo-Optical Methods.

Figure 7:
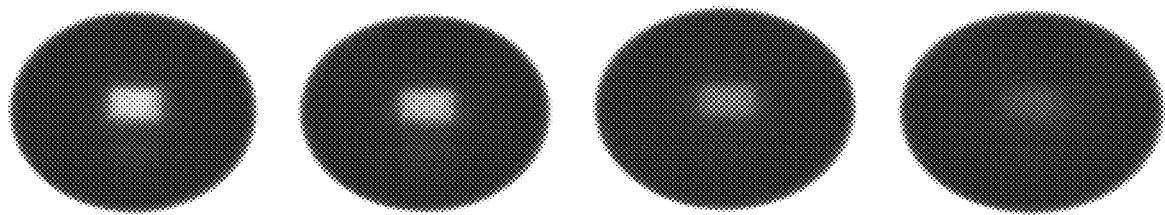
FIG. 7 depicts a representative sequence of levitating blood plasma drop images during the onset of coagulation, used for photo-optical measurements.
Figure 8:
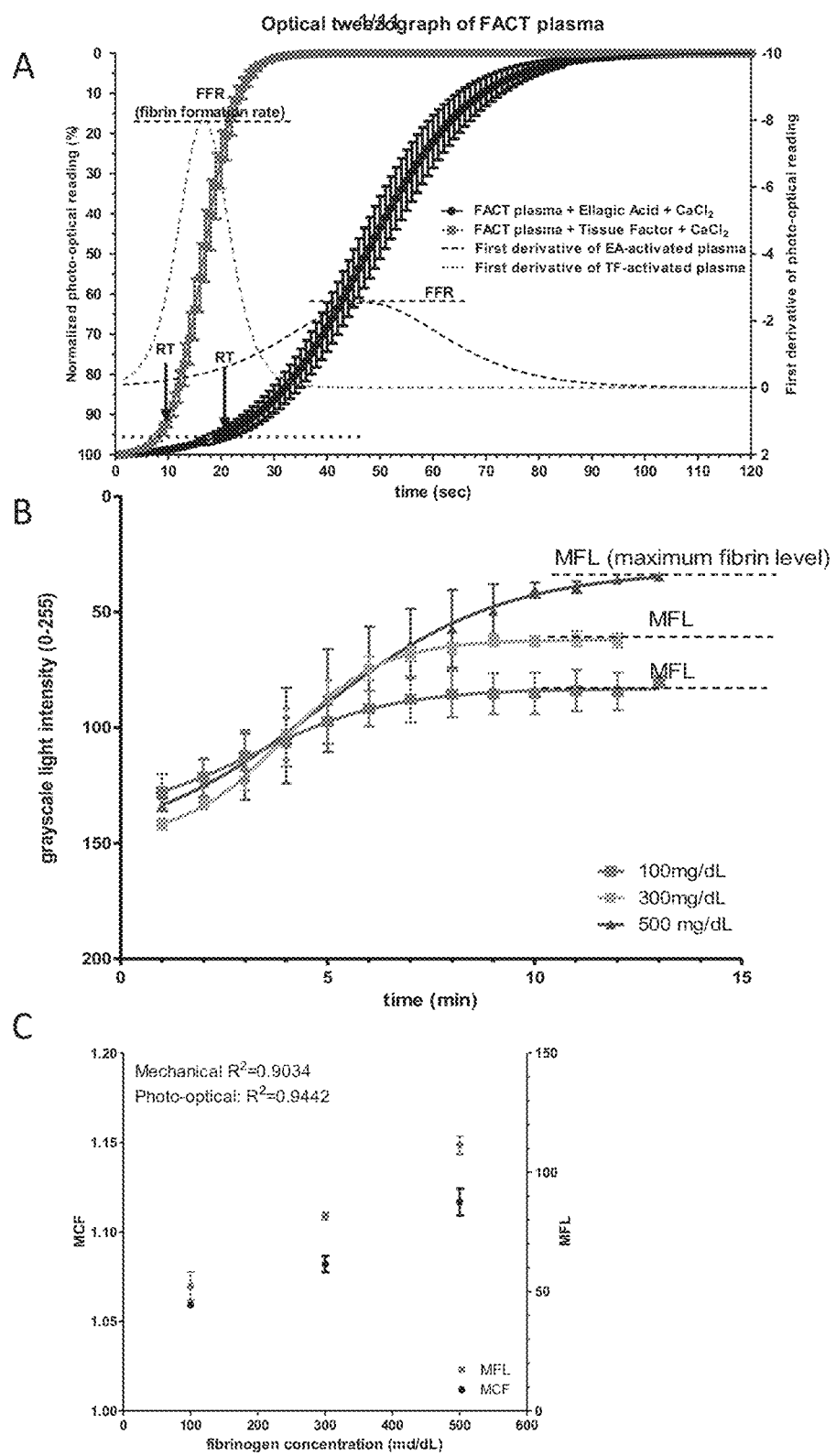
FIG. 8A depicts the photo-optical tweezograph of Factor Assay Control Plasma (FACT) samples exposed to ellagic acid, showing measurement of RT and FFR.
FIG. 8B depicts the photo-optical tweezograph of blood plasma samples with fibrinogen levels of 100, 300, and 500 mg/dL, indicating an increase in MFL with fibrinogen concentration.
FIG. 8C depicts significant correlation of fibrinogen concentration with MCF ($R^2$=0.90) and MFL ($R^2$=0.94).

In this Example, uniform soft light was applied to the central part of a levitated sample drop (as is shown in FIG. 7), using a levitated sample and photo-optical tweezing, as was described above. In this Example, the sample drop was injected into the system as previously described, and maintained at defined aspect ratio (1.2-1.3). The image acquisition rate was adjusted to 1 FPS for 3-10 minutes. The average light intensity of the sample center area was determined from acquired images using the edge detection method, grey scale reading functions including pixel density reading and central node detection. Similar to a mechanical tweezograph, the average light intensity was plotted as a function of time, leading to a sigmoid shape curve (photo-optical tweezograph).

Factor assay control (FACT) plasma, purchased from George King Bio-Medical (Overland Park, Kans.), and high fibrinogen control and low fibrinogen control plasma samples, purchased from Fisher Scientific (Hampton, N.H.) were used in these experiments. Commercial PT/aPTT activators and re-calcification solution were purchased from Thermo Fisher Scientific to reproduce the conditions used in commercial coagulation analyzers for PT and aPTT tests. For comparative analysis, this Example also features the unique air-triggered method to measure blood coagulation.

Results.

The photo-optical tweezographs of coagulating blood plasma from this Example are shown in FIGS. 8A-8C. The tweezographs were normalized to 100% and the RT was defined as the time when the light intensity (in this case, darkness) reached 5% of its maximum value.

One implementation of the disclosed ATPA method predicts that the TF-activated plasma samples start coagulation, on average, at RT=13 sec (FIG. 8A), while the manufacturer range of PT values for these samples is 11-14 sec. The implementation further predicts that the ellagic acid-activated plasma samples start coagulation, on average, at 27 sec, which is within the range of aPTT values (25-35 sec) provided by the manufacturer. It is understood that at least two kinetic parameters can be measured from these implementations, including: reaction time (RT) and fibrin formation rate (FFR).

FIG. 8B depicts the photo-optical tweezographs of blood plasma samples with fibrinogen concentration of 100, 300, and 500 mg/dL. Maximum fibrin level (MFL) for each group has been measured from photo-optical tweezographs. FIG. 8C depicts significant correlation of fibrinogen concentration with MCF ($R^2$=0.90) and MFL ($R^2$=0.94).

It is understood that the optical reading method (Clauss assay, PT-derived method) is widely used in hospitals for estimation of fibrinogen concentration, along with a viscoelastic method like TEG, which extrapolate fibrinogen level from the clot strength. This Example again established that the APTA is able to accurately measure coagulation parameters such as RT (including PT and aPTT values) and MFL.

Example 8: Development of an Integrated Photo-Optical/Mechanical Measurement of Blood Plasma Coagulation to Estimate the Functional Level of Factor XIII Factor XIII is the enzyme that crosslinks fibrin, thus forming a stabilized fibrin matrix. The Factor XIII deficiency in blood causes the vulnerable clot formation and severe bleeding tendency. Because the Factor XIII deficiency does not affect the fibrin formation process, the RT data such as PT and aPTT values are often within normal ranges. Currently, the concentration of Factor XIII in blood can be measured in specialized hematology laboratories using a very expensive, antibody-based method, and clinicians in hospitals often wait for weeks to get results back from these laboratories. By integrating the mechanical and photo-optical measurements (FIG. 9), the disclosed ATPA method provides a unique and simple way to measure the functional level of Factor XIII in blood samples.

Blood Samples Used in Measurement of Factor XIII Levels.

FACT, Factor XIII deficient plasma and a mixture of FACT and Factor XIII deficient plasmas were used in this experiment. Both photo-optical and mechanical tweezographs were plotted. The time delay between these graphs represents the fibrin network formation time (FNFT).

Results:

FIGS. 10A-B show the photo-optical and mechanical tweezographs of A) FACT and B) Factor XIII deficient plasma, respectively. Specifically, the left axis is for mechanical tweezograph (green line) and the right axis is for photo-optical tweezograph (red line). The FNFT increases from 3.5 min in normal plasma (A) to 4.75 min to Factor XIII deficient plasma (B). Thus, this parameter can be used to detect the functional level of Factor XIII.

Example 9: Application of the ATPA Method to Commercial Human Plasma Samples Including Factor Assay Control Samples and Plasma Samples with Coagulation Factor Deficiency to Identify the Impact of Single Factor Deficiency on Coagulation Process This Example establishes standard and borderline coagulation curves using commercial factor assay control plasma. From these curves, it is possible to identify the impact of coagulation factors (e.g., fibrinogen, Factors V/VII/X/XII/XIII) and define normal ranges for the following coagulation parameters: reaction time (RT), clot initiation time (CIT), fibrin network formation time (FNFT), time to firm clot formation (TFCF), and maximum clot firmness (MCF).

Figure 9:
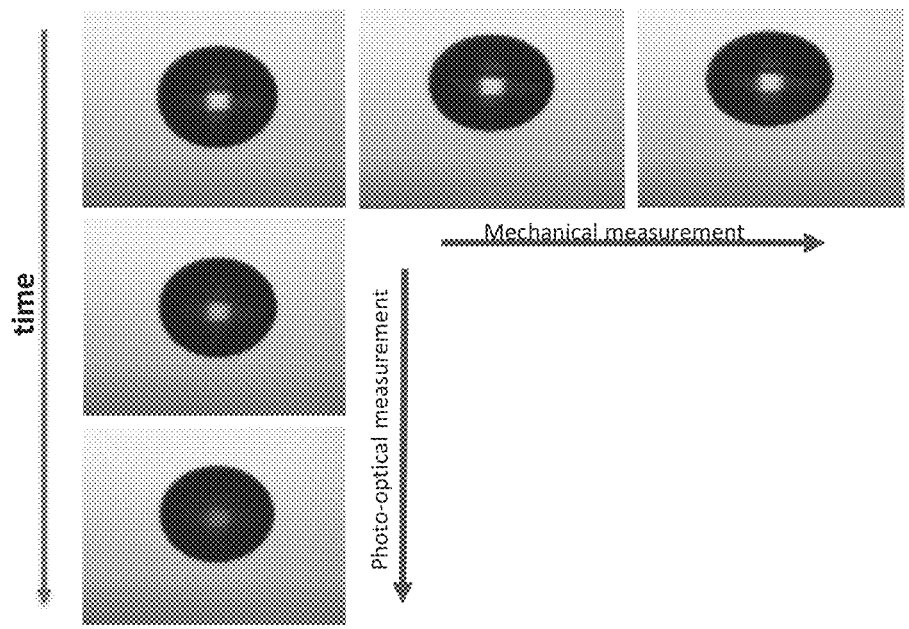
FIG. 9 depicts the illustration of integrated photo-optical and mechanical measurement on a blood plasma drop.

Methods:

Based on the preliminary fibrinogen and Factor XIII data shown in FIG. 9, it was anticipated that the ATPA method is sensitive enough for identify specific factor deficiency of blood plasma. In this Example, every 1 or 2 minutes, a sequence of photos of the blood plasma sample drop under quasi-static acoustic tweezing were recorded to obtain bulk deformability at different time points. The photo-optical intensity data was obtained from the same sequence of images.

Figure 11:
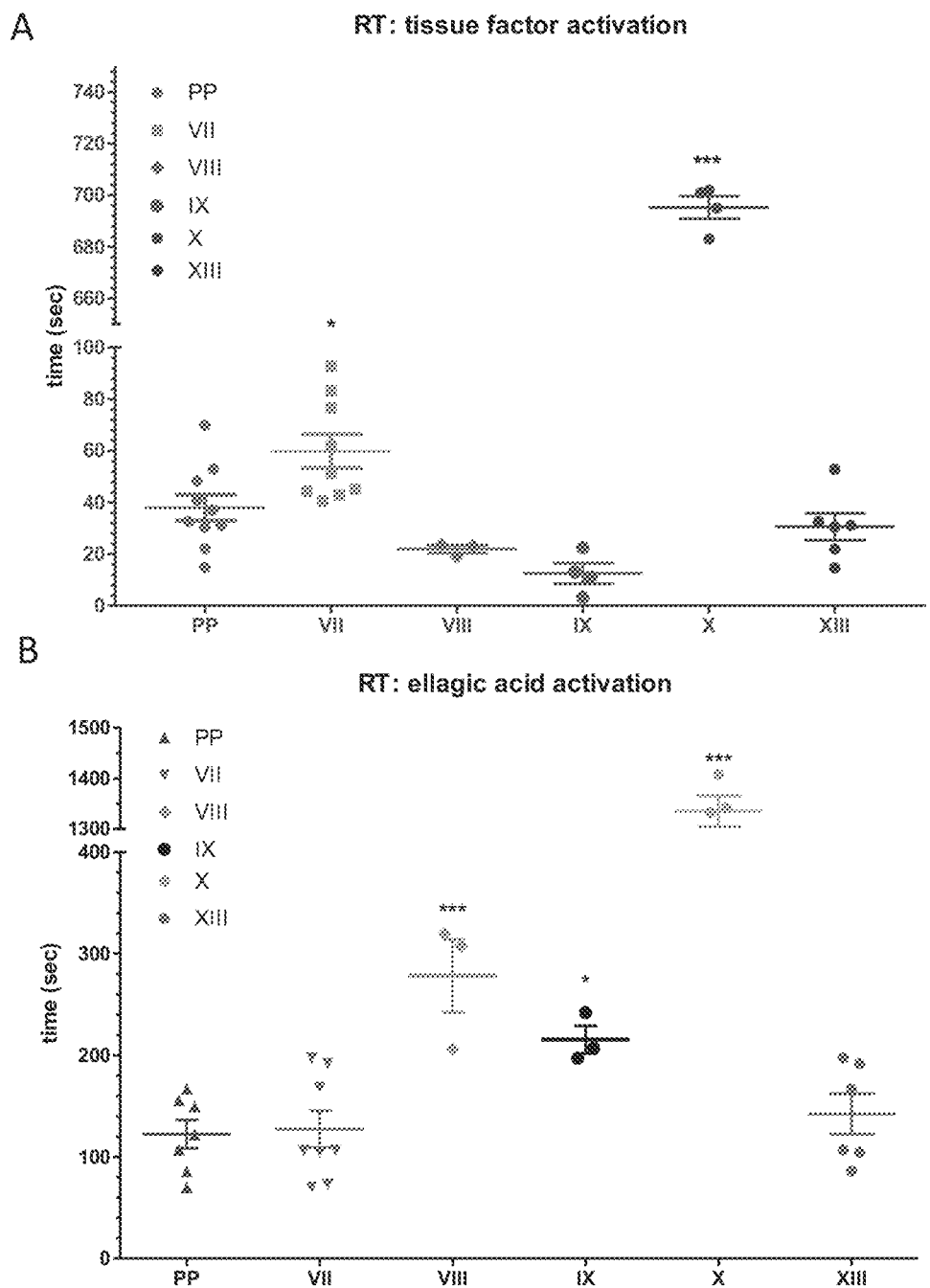
FIGS. 11A-11B depict the RT measurement of pooled plasma (PP) as well as Factor VII-, Factor VIII-, Factor IX-, Factor X-, and Factor XIII-deficient plasma from photo-optical tweezographs.

Results:

FIGS. 11A-11B depict the RT of pool plasma (PP) and Factor VII-, Factor VIII-, Factor IX-, Factor X-, and Factor XIII-deficient plasma. In FIG. 11A, the factor deficient plasma samples were exposed to tissue factor (PT test, extrinsic pathway of coagulation). In FIG. 11B, the factor deficient plasma samples were exposed to ellagic acid (aPTT test, intrinsic pathway of coagulation). Factor VII- and Factor X-deficient plasma samples showed a significant prolonged PT, as compared to PP samples, indicating a slow response to the extrinsic pathway of coagulation (vascular trauma) and thus a high risk of bleeding during trauma. Factor VIII-, Factor IX-, and Factor X-plasma showed a significant prolonged aPTT, as compared to PP samples, indicating a slow response to the intrinsic pathway of coagulation (blood contact with collagen or dysfunctional endothelium). Both PT and aPTT are prolonged in Factor X-deficient plasma, indicating a risk of excessive bleeding.

DISCUSSION

The Examples of the ATPA method show that the various implementations of the disclosed acoustic tweezing-based photo-optical method can accurately measure the reaction time and fibrinogen levels in blood plasma. The Examples of the ATPA method also demonstrate that the MFL and MCF increase with an increase in the fibrinogen concentration.

The disclosed Examples of the ATPA method also show that the disclosed acoustic tweezing-based photo-optical method can accurately measure the reaction time, including PT/aPTT values, and fibrinogen levels in blood plasma. It also demonstrates that the MFL and MCF increase with an increase in the fibrinogen concentration.

The disclosed Examples of the ATPA method also show that the disclosed ATPA method can identify functional deficiencies of coagulation factors such as Factors VII, VIII, IX, and X and is an unique method to measure the functional level of Factor XIII in blood samples.

The integrated photo-optical and mechanical test is performed on the same sample drop during its levitation in the acoustic tweezing device. The data indicate that this integrated test provide the information about coagulation parameters (including the MCF) within 10 minutes (while current devices requiring at least 30 minutes) using the sample volume of just 4 microliters (~100 times less than the sample volume required in available coagulation analyzers).

The disclosed embodiments of the ATPA method can also be used in the chemical and pharmaceutical industries, e.g., for cross-linked polymer formulations. Similarly, the method can be used to assess the effects of various cross-linkers or cross-link breakers/inhibitors (used as drugs for treatment of fibrous disorders, cancer, neurodegenerative conditions) on the mechanical properties of soft biological tissues.

In various implementations, the ATPA method uses a small volume of blood (~4 µL) and robust coagulation measurements compared to currently available contact techniques. In addition to whole blood analysis, the various implementations of the ATPA can monitor blood plasma coagulation status by both photo-optical and mechanical techniques. For example, by integrating photo-optical and mechanical measurements the time delay between fibrin formation and coagulation was determined, referred to as fibrin network formation time (FNFT).

The disclosed implementations of the ATPA method feature a variety of improvements over the prior art. In various implementations, the non-contact ATPA technology is able to measure the rheological properties of sample fluids over time and can provide a unique assay for evaluation of polymerization kinetics of sample fluids and coagulation status of whole blood and blood plasma via a combination of photo-optical and mechanical tests.

In certain implementations, the disclosed ATPA method can create an air or liquid contact only environment via levitating a sample drop with acoustic radiation pressure. The information about fluid polymerization kinetics is obtained by measuring changes in deformability of a levitating fluid sample with time.

In certain implementations, the disclosed ATPA method can measure changes in deformability of whole blood or blood plasma samples, and generate a mechanical tweezograph reflecting the coagulation status of blood samples.

In certain implementations, the disclosed ATPA method is modified with integrated photo-optical and mechanical methods and can provide a unique bridge to perform two different types of assays on one blood drop, thus identify the abnormality of coagulation status.

In one embodiment, the disclosed implementations allow for the measurement of the reaction time of blood and other kinetic parameters of blood coagulation without exposing the blood sample to artificial reagents or inducing sample contact with artificial surfaces. This provides more natural environment for blood coagulation and thus makes the disclosed implementations more accurate in the assessment of a risk of bleeding or thrombosis than currently available blood coagulation assays. Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Although the disclosure has been described with reference to certain embodiments, persons skilled in the art will recognize that changes may be made in form and detail without departing from the spirit and scope of the disclosed apparatus, systems and methods.

What is claimed is:

1. A noncontact, acoustic-tweezing method of measuring time-dependent rheological and polymerization properties of a sample comprising:
   a. levitating the sample;
   b. modulating the amplitude of acoustic pressure applied to the sample so as to induce deformation;
   c. capturing at least one image of the sample;
   d. collecting at least one photo-optical measurement and at least one mechanical measurement from the captured images of the levitating sample during deformation;
   e. determining at least one rheological property of the sample; and
   f. determining at least one kinetic property of sample polymerization,
   wherein the determined kinetic properties of sample polymerization:
   i. comprise polymer network formation time measured by the time difference between the time to maximum polymerization rate in a mechanical tweezograph and the time to maximum monomer formation rate in a photo-optical tweezograph, and
   ii. are selected from the group consisting of: photo-optical tweezograph, mechanical tweezograph, reaction time, monomer formation rate, maximum monomer level, polymerization onset, polymerization rate, polymerization time, gel firmness and polymer network formation time.

2. A noncontact, acoustic-tweezing method of measuring time-dependent rheological and polymerization properties of a sample comprising:
   a. levitating the sample;
   b. modulating the amplitude of acoustic pressure applied to the sample so as to induce deformation;
   c. capturing at least one image of the sample;
   d. collecting at least one photo-optical measurement and at least one mechanical measurement from the captured images of the levitating sample during deformation;
   e. determining at least one rheological property of the sample;
   f. extracting coagulation kinetics data; and
   g. evaluating a functional level of fibrinogen from at least one of RT, MFL, MCF, and FNFT data extracted from the at least one photo-optical measurement and at least one mechanical measurement.

3. A noncontact, acoustic-tweezing method of measuring time-dependent rheological and polymerization properties of a sample comprising:
   a. levitating the sample;
   b. modulating acoustic pressure amplitude applied to the sample so as to induce deformation;
   c. capturing at least one image of the sample;
   d. collecting at least one photo-optical measurement and at least one mechanical measurement from the captured images of the levitating sample during deformation;
   e. determining at least one rheological property of the sample;
   f. extracting coagulation kinetics data, and
   g. evaluating a functional level of Factor XIII from at least one of RT, MFL, MCF, and FNFT data extracted from the photo-optical and mechanical tweezographs.

4. A noncontact, acoustic-tweezing system for measuring time-dependent rheological and polymerization properties of a sample comprising:
   a. levitator configured to levitate the sample;
   b. an amplitude modulator configured to modulate acoustic pressure applied to the sample so as to induce deformation;
   c. a camera configured to capture at least one image of the sample and generate captured images; and
   d. a data acquisition system configured to:
      i. collect:
         A. at least one photo-optical measurement of the sample; and
         B. at least one mechanical measurement of the sample during deformation from the captured images, and
      ii. determine at least one rheological property of the sample,
   wherein:
   i. the data acquisition system is configured to determine at least one kinetic property of sample polymerization,
   ii. the determined kinetic properties of sample polymerization are selected from the group consisting of: photo-optical tweezograph, mechanical tweezograph, reaction time, monomer formation rate, maximum monomer level, polymerization onset, polymerization rate, polymerization time, gel firmness and polymer network formation time, and
   iii. the polymer network formation time is the time difference between reaching the maximum polymerization rate in a mechanical tweezograph and reaching the maximum monomer formation rate in a photo-optical tweezograph.

5. A noncontact, acoustic-tweezing system for measuring time-dependent rheological and polymerization properties of a sample comprising:
   a. levitator configured to levitate the sample;
   b. an amplitude modulator configured to modulate acoustic pressure applied to the sample so as to induce deformation;
   c. a camera configured to capture at least one image of the sample and generate captured images; and
   d. a data acquisition system configured to:
      i. collect:
         A. at least one photo-optical measurement of the sample; and
         B. at least one mechanical measurement of the sample during deformation from the captured images, and
      ii. determine at least one rheological property of the sample, wherein:
   i. the one or more rheological property is selected from the group consisting of:
   elastic modulus, shear elasticity, shear viscosity, dynamic modulus, storage modulus, and loss modulus, and
   ii. the fibrin network formation time (FNFT) is the time difference between reaching the maximum clotting rate (CR) in a mechanical tweezograph and reaching the maximum fibrin formation rate (FFR) in a photo-optical tweezograph.

* * * * *